(12) United States Patent
Schwob

(10) Patent No.: US 7,515,720 B2
(45) Date of Patent: Apr. 7, 2009

(54) METHOD AND DEVICE FOR ADAPTING HEARING AIDS

(75) Inventor: Christoph Schwob, Muttenz (CH)

(73) Assignee: Audiocare AG, Pratteln (CH)

( * ) Notice: Subject to any disclaimer, the term of this patent is extended or adjusted under 35 U.S.C. 154(b) by 0 days.

(21) Appl. No.: 10/580,637

(22) PCT Filed: Nov. 11, 2004

(86) PCT No.: PCT/CH2004/000682

§ 371 (c)(1),
(2), (4) Date: Mar. 13, 2007

(87) PCT Pub. No.: WO2005/055651

PCT Pub. Date: Jun. 16, 2005

(65) Prior Publication Data

US 2007/0217636 A1    Sep. 20, 2007

(30) Foreign Application Priority Data

Dec. 1, 2003    (CH) .................................. 2046/03

(51) Int. Cl.
H04R 29/00    (2006.01)
H04R 25/00    (2006.01)

(52) U.S. Cl. ........................ 381/60; 361/312

(58) Field of Classification Search .................... 381/72, 381/312, 317, 314, 60; 700/94
See application file for complete search history.

(56) References Cited

U.S. PATENT DOCUMENTS 7,288,072 B2 * 10/2007 Stott et al. ................... 600/559
2003/0099370 A1 * 5/2003 Moore ......................... 381/312

FOREIGN PATENT DOCUMENTS

DE    4339898 A1    6/1995
DE    19904044 A1   7/2000
FR    2664494 A1    1/1992

* cited by examiner

Primary Examiner—Vivian Chin
Assistant Examiner—George C Monikang
(74) Attorney, Agent, or Firm—Hammer & Associates, P.C.

(57) ABSTRACT

A method for adapting hearing aids to the individual requirements of a hard-of-hearing patient in situations which are close to reality, wherein an example of a sound and a scene corresponding to said example of a sound are optically indicated to a patient such that the visual impression thereof is also taken into account in order to judge the acoustic result. A suitable device therefor comprises an enclosed area with room for a specialist to carry out the adaptation and room for a patient, a monitor being provided in both places, in addition to a computer which is used by the specialist to carry out said adaptation and which provides the monitors with video sequences.

2 Claims, 1 Drawing Sheet

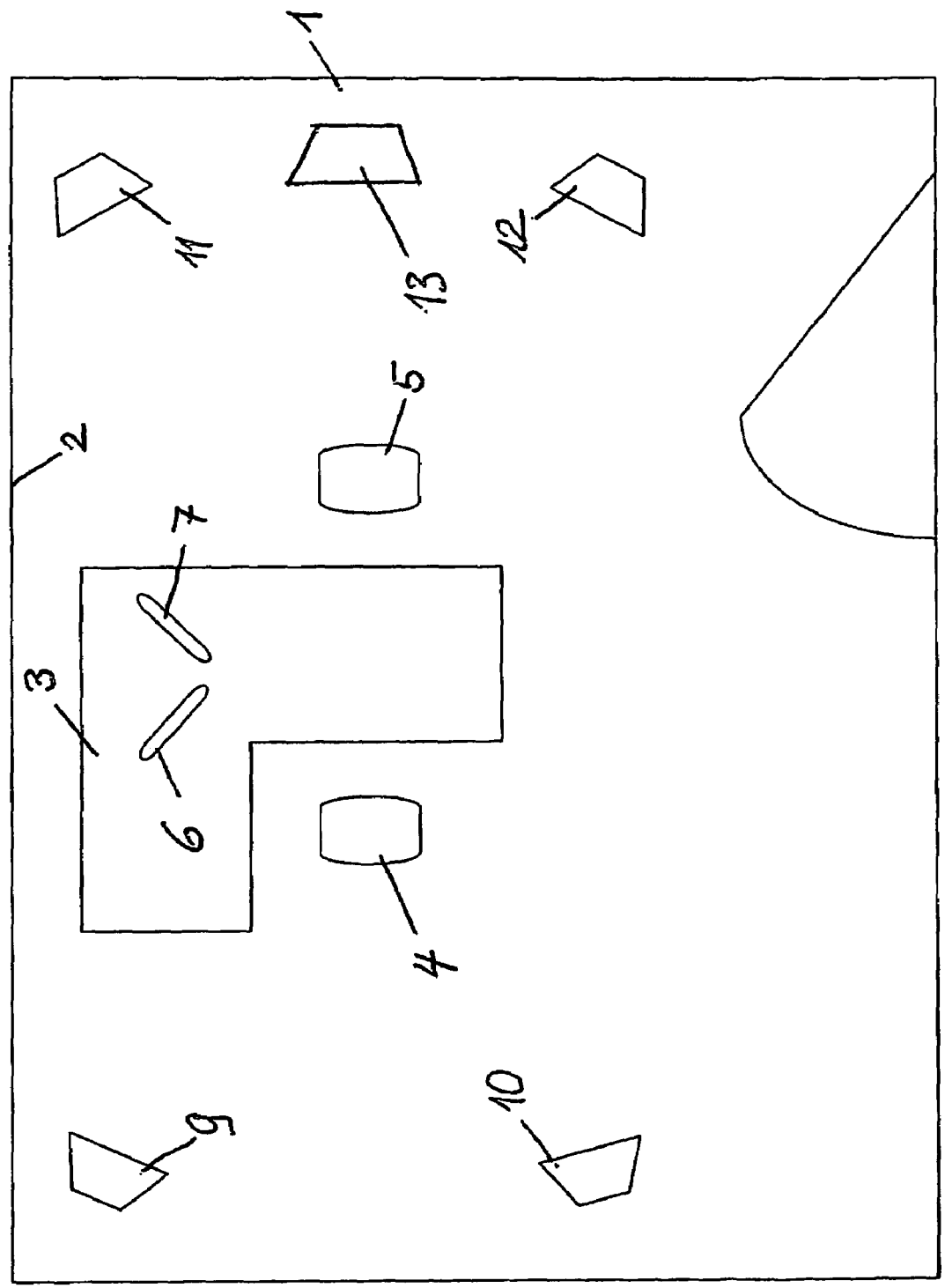

METHOD AND DEVICE FOR ADAPTING HEARING AIDS

The invention relates to a method for matching hearing aids to the individual requirements of a patient with impaired hearing in realistic situations, and to a device for carrying out the method.

Hearing aids have become more complex in the recent past and offer a large number of adjustment options. In-situ measurements, loudness scaling, speech audiometry with or without interference noise indicate the performance of the hearing aids to the specialist. In contrast, however, the requirements of those with impaired hearing always remain the same: to hear and understand better, and in particular even in a noisy environment. In this case, it is irrelevant to those with impaired hearing how technically complex the design of the hearing aid is. Only the detectable usefulness in their personal environment is important to them, that is to say their own hearing experience in realistic situations.

At the same time, modern hearing aids have various characteristics which can neither be made use of nor measured in a quiet matching room. They likewise always behave completely differently, depending on the personal lifestyle of the person wearing the hearing aid.

Nevertheless, until now, it has been normal practice to carry out the matching process in quiet situations, as a result of which hearing situations for the individual person with impaired hearing can be simulated only inadequately.

Admittedly, this method is technically complex. However, it can be carried out and can be optimally reproduced within a normal session duration.

There are various methods for introducing sound examples in the matching room. A number of compact disks are commercially available. In addition, the hearing-aid manufacturers offer matching devices which have the capability to play noise examples.

However, when using such sound examples in the matching room, it has been found that those with impaired hearing (and a large number of those with normal hearing as well) cannot identify noises and therefore cannot produce any reference at all. For example, when only noises are being played, it is always necessary to explain what is happening in this sound example. However, said explanations are useful only to a limited extent: on the one hand, for example the interference sound level in the case of a road scene is changing all the time, and on the other hand many of those with impaired hearing do not know the scenes being played to them or maintain that they are never subject to noise environments such as these.

If different hearing-aid settings or hearing aids are compared, the person with impaired hearing frequently does not identify the same sound examples again.

Furthermore, matching in real situations relates not only to the simulations of sounds and noises but additionally and highly importantly to the understanding of speech in noisy situations. Text recordings have not been proven for this purpose. On the one hand, the person with impaired hearing very quickly learns the content by heart and on the other hand these texts, which are generally recorded in a quiet environment, do not match the various sound examples in terms of volume and the sound of the voice.

The invention is based on the object of providing a capability of overcoming these disadvantages of the previously normal hearing-aid matching process and for carrying out this realistically and reproducibly for the individual patient in different acoustic environments.

According to the invention, this object is achieved in that a sound example and scene which corresponds to the sound example is passed visually to the patient at the same time, in order that the visual impression can also be used for assessment of the acoustic experience. The patient is preferably confronted with video recordings of a number of typical life situations with a different noise intensity and composition.

The videos should be reproduced with as natural a sound as possible. The matching room is therefore preferably equipped with good loudspeakers which are positioned so as to allow a surround sound effect. Furthermore, it is advantageous to use recordings which give the effective impression of the real hearing experience in terms of the spatial imaging. These recordings are recorded using two special microphones which the operator which is operating the camera and is making the video recordings is fitted with in his two auricles or auditory passages. This results in an optimally realistic recording, with this technique being referred to as bi-authentic technology.

It is also advantageous for the scenes to be repeatable quickly and easily. This allows use for comparison of different programs or different hearing aids. If longer scenes were used, too many changes would occur in the level and frequency components, thus no longer allowing comparability.

With regard to speech comprehensibility in noisy situations, a conversation preferably takes place between the specialist for the matching process and the patient who is wearing the hearing aid. For this purpose, the specialist for the matching process is preferably likewise in the same sound situation in order to correctly adapt his or her voice. He or she must also be able to hold a conversation on widely differing subjects since it is not sufficient to just continually ask about the volume of disturbing interference noise etc.

The capability to remember what has been heard is very short. It is therefore advantageous to be able to change between hearing-aid settings or programs while playing the video. The method is manufacture-independent and allows comparative matching by means of absolutely identical scenes.

One exemplary embodiment of a suitable matching room will be described in the following text with reference to the attached drawing. A room 1 has an area of about 10 square meters and has no special sound-absorbing walls etc. The room therefore has a reverberation time which corresponds to that of a normal living room or work room. A spatial sensitivity is thus achieved by sufficient diffuseness.

A table 3 is arranged adjacent to one wall 2, preferably approximately at its center. A chair 4 for the specialist for the matching process and who is carrying out the matching process is located on one side of the table. A further chair 5 for the patient for whom a hearing aid is being matched is located on the opposite side of the table.

A monitor 6 facing the specialist for the matching process and a further monitor 7 facing the patient's location are located on the table. With regard to the seating positions and the direction of the monitors, it may be advantageous in particular for the patient not to be able to see the monitor 6 for the specialist for the matching process. Both monitors are connected to a computer 8, which is operated by the specialist for the matching process.

Two loudspeakers 9, 10 are arranged at a distance from one another behind the location 4 for the specialist for the matching process. Two further loudspeakers 11, 12 are located at a distance from one another behind the location 5 of the patient. Furthermore, a low-tone loudspeaker 13, a so-called sub-woofer, is arranged behind the patient's location. If four broadband loudspeakers are used, there is no need for the sub-woofer. These five loudspeakers are driven by a so-called surround amplifier in the computer and produce a sound field which is associated with a video recording being played back on the monitors.

Many years of evaluations of reports of experiences which those with impaired hearing have reported from everyday use after wearing hearing aids for trials purposes have resulted in groups of hearing situations. Expedient groups are listed in the following text, and are in each case associated with examples of video sequences:

Individual noises:
    pages of a newspaper
    vacuum cleaner
Interference noises:
    road traffic
    restaurant
At home:
    clearing away cutlery
    banging plates
Environment:
    inside a museum
    market stores
Natural:
    twittering of birds
    a stream
Driving:
    in a car
    on the roadway
Music:
    various styles
Hearing situations in the workplace:
    supermarket checkouts
    construction machine The films are driven using software which allows the films to be called up very quickly. Film control always remains "on-top", so that films can be played back independently of other software programs.

The films can thus be used for programming all hearing aids, independently of the manufacturer. The matching process takes place as described in the following text. Before matching a hearing aid to an individual, a conventional basic setting is applied on the basis of audiometry and in-situ measurement.

The in-situ measurement is used for basic programming of the gain and output power of the hearing aid. The gain is adjusted in a first step. Dynamic response is then adjusted by means of DSL.

Each hearing aid is set using this method for the comparative matching process. This means that the hearing aids have a largely similar volume in a quiet room, and sound approximately the same. If the initial setting alone were to be used on the basis of the fitting tool this would not result in any hearing-aid comparison but in a comparison of the prior calculation methods. During the comparative matching process, this would not result in the best tailoring of the hearing aid that is most suitable for the patient, but in that for which the initial setting randomly turns out to be "pleasantest". A correct comparison can be carried out only by means of a manufacturer-independent method.

A commercially available in-situ measurement system can be used to carry out measurements with so-called "extreme noise". This makes it possible to check the operation of the hearing aids by means of stimulation with natural signals. This can also be extremely helpful, in particular for the use of interference noise suppression techniques and the checking of their effectiveness.

The in-situ basic programming is then followed by individual matching in a series of steps. The videos are selected and presented by the specialist for the matching process on the basis of the hearing profile as defined at the start of the matching process (analysis of the personal hearing requirements).

The specialist for the matching process listens to a number of examples together with the hearing-aid wearer and corrects the adjustment until the subjective impression of the volume balance is correct.

A number of examples are listened to jointly, and the hearing-aid programming is corrected on the basis of the subjective sound assessment.

Speech comprehensibility in a quiet environment is assessed by the specialist for the matching process conversely with the hearing-aid wearer in the quiet matching room. In order to access speech comprehensibility with interference noise, the specialist for the matching process converses with the hearing-aid wearer in various situations with interference noise. The various interference noise situations are selected on the basis of the hearing profile. During this process, different settings with regard to sound, interference noise suppression techniques, directional microphones, etc. can be compared with one another, and the best version can be selected.

One scene lasts for a maximum of about 60 seconds. It is thus also possible to compare different hearing aids or systems in a short time by direct comparisons of pairs. The reproducibility of the situation clearly emphasizes the differences between the systems. In addition to the comparison of the various signal processing modes, the comparisons of pairs also allow immediate assessment of different strategies such as multiple program technologies versus full automation, etc.

The next step is to jointly listen to music. Various areas can be covered here. In addition to good sensitivity for that type of music which personally suits the hearing-aid wearer and is presented at room volume, it is also possible to check the tolerance to loud music here.

In the case of hearing aids with a plurality of programs, the described steps are carried out in the hearing-aid programs which are in each case matched to the scenes. The major advantage here according to the invention is that the usefulness of these programs can be made immediately audible. In this case, by way of example, a conversation in a restaurant is started with a ball microphone without any interference noise suppression, followed by switching to a second program with a directional microphone, etc.

The procedure with basic programming by means of in-situ measurement (optimization to intended frequency responses) and the subsequent steps with the matching process according to the invention make it possible to compare hearing aids quickly and reproducibly. Real comparison is possible because the procedure is always the same. This also applies to digital hearing aids, the method is particularly advantageous for digital, self-regulating hearing aids. These hearing aids behave differently all the time in daily use by the customer and situations which are supposedly the same are never actually the same from the physical point of view. The person with impaired hearing can form an opinion about the various hearing aids only by means of a rapidly reproducibly sound environment, and for trials use in an everyday environment chooses that solution which is the most promising for him or her. The risk of the hearing aids being found to be unsuitable in everyday use is considerably reduced by the use of interference noises in the matching room.

The method according to the invention also optimally includes the subjective impression of the person with impaired hearing. This results in better satisfaction in terms of the sound behavior of the hearing aids.

Automatic hearing aids and those with a plurality of programs can neither be introduced nor programmed in the best possible way without the presentation of different acoustic environments. This is a necessary precondition for the matching of hearing aids from these two groups, that is to say for the vast majority of the currently available digital hearing aids. As a result of the direct comparison of a plurality of hearing aids in identical situations, the hearing-aid wearer knows that the best hearing aids for him or her have been selected. The method according to the invention likewise makes it possible to indicate the advantages of the various supplies: binaural in comparison to monaural; supply on one side for those with normal hearing in one ear; high-tone supply; CROS, BICROS. A person with impaired hearing in this context could neither experience the usefulness of the hearing aids nor could the hearing aid settings be optimized in quiet rooms.

In addition, the patient can be shown the advantages of technically high-performance hearing aids in comparison to simple versions.

The method according to the invention is also a major aid to the training of hearing-aid wearers with regard to the behavior in different acoustic environments. For example, together with the specialist for the matching process, programs can be interchanged and the changes can be experienced directly in this process.

The invention claimed is:

1. A method for matching hearing aids to the individual requirements of a patient with impaired hearing in realistic situations, comprising the steps of:
   providing two monitors, one for a specialist and one for said patient, a computer and at least one speaker where said computer supplies said two monitors with a video sequence and said speaker with a sound example;
   passing said sound example and scene which corresponds to said sound example visually to said patient at the same time, in order that a visual impression can be used for assessment of the acoustic experience by said specialist for matching a hearing aid to a patient's individual requirements.

2. The method for matching hearing aids to the individual requirements of a patient with impaired hearing in realistic situations as claimed in claim 1, further comprising the steps of:
   providing a closed room with a place for the specialist for a matching process,
   having a monitor facing the specialist and
   having a patient space with a monitor facing the patient, where said computer which supplies the two monitors with video sequences that can be operated by the specialist for the matching process.

* * * * *